United States Patent [19]

Hidasi et al.

[11] Patent Number: 4,845,126
[45] Date of Patent: Jul. 4, 1989

[54] INSECTICIDAL COMPOSITION COMPRISING MORE THAN ONE ACTIVE INGREDIENT

[75] Inventors: György Hidasi, Budapest; Istvan Szekely, Dunakeszi; Bela Bertok; Sandor Zoltan, both of Budapest; Lajos Nagy, Szentendre; Antal Gajari, Budapest; Eva Somfai, Budapest; Agnes Hegedus, Budapest; Laszlo Pap, Budapest; Rudolf Soos, Budapest; Erzsebet Radvany, Budapest; Sandor Botar, Budapest; Tamas Szabolcsi, Budapest, all of Hungary

[73] Assignee: Chinoin Gyogyszer es Vegyeszeti Termekek Gyara Rt., Budapest, Hungary

[21] Appl. No.: 916,546
[22] PCT Filed: Jan. 16, 1986
[86] PCT No.: PCT/HU86/00004
 § 371 Date: Oct. 15, 1986
 § 102(e) Date: Oct. 15, 1986
[87] PCT Pub. No.: WO86/04216
 PCT Pub. Date: Jul. 31, 1986

[30] Foreign Application Priority Data

Jan. 16, 1985 [HU] Hungary .................. 158/85
Jan. 8, 1986 [HU] Hungary .................. 74/86

[51] Int. Cl.⁴ .......................................... A01N 37/34
[52] U.S. Cl. ................................................ 514/521
[58] Field of Search ...................................... 514/521

[56] References Cited

U.S. PATENT DOCUMENTS

| | | | |
|---|---|---|---|
| 4,024,163 | 5/1977 | Elliott et al. | 514/521 |
| 4,031,239 | 6/1977 | Schrider | 514/521 |
| 4,181,735 | 1/1980 | Smolikowski et al. | 514/521 |
| 4,404,223 | 9/1983 | Matthewson | 514/521 |
| 4,524,150 | 6/1985 | Adalsteinsson | 514/521 |

FOREIGN PATENT DOCUMENTS

| | | | |
|---|---|---|---|
| 0174739 | 3/1986 | European Pat. Off. | 514/521 |
| 2402411 | 5/1979 | France | 514/521 |
| 56-57755 | 5/1981 | Japan | 514/521 |
| 56-57756 | 5/1981 | Japan | 514/521 |

*Primary Examiner*—Allen J. Robinson
*Attorney, Agent, or Firm*—Herbert Dubno; Jonathan Myers

[57] ABSTRACT

According to the present invention there is provided a synergistic insecticidal composition containing more than one active ingredients and being harmless to environment characterized by comprising in an amount of from 0.001 to 99% by weight a synthetic pyrethroid of the Formula /I/

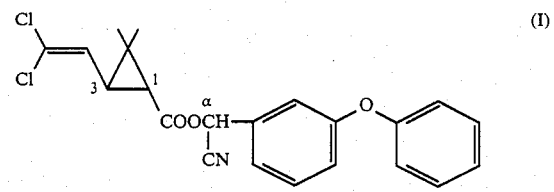

namely substantially only the 1RtransS and 1StransR entantiomer-pair /Ib/ out from the possible eight isomers—optionally in admixture with an amount of up to 100% by weight of one or more activator/s/ and auxiliary agent/s/, particularly antioxidants, stabilizing agents, wetting agents, emulsifying agents, dispersing agents, antifoam agents, dileunts and/or fillers.

The enantiomer-pair Ib consisting of the 1RtransS and 1StransR isomers is new and the invention also relates to the said new enantiomer-pair and a process for the preparation thereof.

The advantage of the insecticidal composition of the present invention is that it is less toxical towards warm-blooded animals and useful parasites and is therefore much less harmful to the environment.

3 Claims, No Drawings

INSECTICIDAL COMPOSITION COMPRISING MORE THAN ONE ACTIVE INGREDIENT

CROSS REFERENCE TO RELATED APPLICATIONS

This application is a national phase of PCT/HU86/00004 and is related to PCT/HU 86/00003, filed 16 January 1986 and based upon Hungarian 158/85 of 16 January 1985 and 74/86 of 8 January 1986.

FIELD OF THE INVENTION

This invention relates to insecticidal compositions comprising more than one pyrethroid active ingredient of the Formula /I/

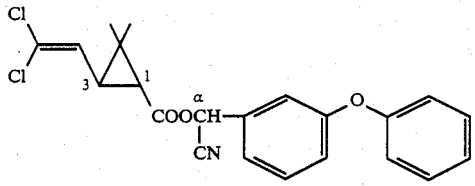

the use thereof, the active ingredients and a process for the preparation of the same.

BACKGROUND OF THE INVENTION

In the present specification the spatial configuration of the substituents related to the chiral carbon atom denoted with "α" is characterized by "S" and "R", respectively. The designations "cis" and "trans", respectively, mark the position of the substituents attached to carbon atom "3" of the cyclopropane ring related to the spatial configuration of the substituents of carbon atom "1". The absolute spatial configuraton of the substituent attached to carbon atom "1" is denoted with the prefix "1R" and "1S", respectively.

In the present specification the various enantiomers and enantiomer-pairs are designated with the following abbreviations:

Ia: mixture of 1RcisS and 1ScisR
Ib: mixture of 1RtransS and 1StransR
Ic: mixture of 1RcisR and 1ScisS
Id: mixture of 1RtransR and 1StransS
If: 1RcisS
Ig: 1RtransS
Ih: 1ScisR
Ii: 1StransR It is known that pyrethroids of the Formula /I/ (known under the generic name "cypermethrin") belong to the valuable family of synthetic pyrethroids and are useful as insecticide (Hungarian Pat. No. 170,866). These compounds may be prepared by reacting m-phenoxy-benzaldehyde cyanohydrine with the corresponding cyclopropane carboxylic acid chloride in the presence of a base [Pestic. Sci. 6, 537, . . . 1975]. The product thus obtained consists of eight stereoisomers i.e. of a mixture of four enantiomer-pairs. If a 60:40 mixture of the corresponding trans and cis cyclopropane carboxylic acid chlorides is used, the mixture contains 18–19% of enantiomer-pair Ia, 21–22% of enantiomer-pair Ic, 26–27% of enantiomer-pair Ib and 33–34% of enantiomer-pair Id.

According to prior art the steroisomers of cypermethrin show different biological activity. It is generally accepted that the activity of molecules comprising cis cyclopropane carboxylic acids is superior to that of the corresponding trans derivatives [Pest. Sci. 7, 273, 1976].

In the comparative biological tests of various pyrethroids [Pest. Sci. 9, 112–116 1978] the cis and trans stereoisomers—including the cypermethrin stereoisomer-pairs—were evaluated together.

The comparative tests were carried out on *Musca domestica* L. and *Phaedon cochleariae* Fab species. Concerning the chloro derivatives from the trans isoomers activity data of 1RtransS Ig and 1RtransR were disclosed. The said data show that—while the 1RtransS isomer possesses a strong activity—the 1RtransR isomer is considerably less active [according to the test the activity related to bioresmetrine 100 amounts to 1400 and 81, respectively, on *Musca domestica* and to 2200 and 110, respectively, on *Phaedon cochleariae*]. It was disclosed further that the activity of a mixture of both tested isomers was lower than the calculated value. Thus the isomers showed an antagonism rather than the expected synergism and the rate of antagonism amounted to 1.42 and 1.46 on house fly and mustard beetle, respectively.

As a result of the said test and publications the trans isomers and mixtures thereof were pushed to the background of biological interest and research was focused to active cis derivatives and mixtures thereof. This lead to the development of alphamethrin (isomer mixture of 1RcisS and 1ScisR Ia) of the chloro derivatives) and decamethrin [comprising the 1RcisS isomer (If) of the bromo derivatives].

Similar data were set forth for the bromo derivative; on mustard beetle the rate of antagonism amounts to 1.48.

DESCRIPTION OF INVENTION

According to an aspect of the present invention there is provided a synergistic insecticidal composition containing more than one active ingredients and being harmless to environment characterized by comprising in an amount of from 0.001 to 99% by weight of a synthetic pyrethroid of the Formula /I/—namely substantially only the 1RtransS and 1StransR enantiomer-pair (Ib) out of the possible eight isomers—optionally in admixture with an amount of up to 100% by weight of one or more activators and auxiliary agents, particularly antioxidants, stabilizing agents, wetting agents, emulsifying agents, dispersing agents, antifoam agents, diluents and/or fillers.

According to a preferred embodiment of this aspect of the present invention there are provided insecticidal compositions comprising an isomer mixture having a purity of at least 95%.

The said isomer mixture is a new crystalline substance, the physicochemical data thereof being disclosed in the Examples.

The present invention is based on the discovery that isomer-mixture Ib possesses useful and advantageous biological properties. This is surprising even if it is taken into consideration that in the field of pyrethroids of the Formula /I/ extended experimental work was accomplished and a number of publications and patents were published.

Thus the present invention is based on the discovery that when using a combination of the 1RtransS isomer Ig [being the most active trans isomer of the compounds of the Formula /I/]and the 1StransR isomer Ii (among the less active isomers from the remaining seven isomers) no antagonism characteristic of the earlier published isomer-pairs is observed.

Moreover a synergistic effect occurs over the additive effect of the pure Ig and Ii isomers when used per se.

The above recognition enables a new type of selection from the isomers of synthetic pyrethroids in order to develop a new active ingredient type having outstanding properties. The said new active ingredient shows various advantages over hitherto known isomer selections:

lower toxicity on warm-blooded species and humans;
more economical manufacturing process;
smaller damages caused to useful parasites and bees.

A significant and decisive advantage of the isomer-mixture Ib of the present invention is that it causes no allergy and skin diseases which were generaly observed on the use of the corresponding cis cypermethrin isomers of similar activity.

The synergistic activity of the components of the isomer-mixture Ib is so much the more surprising as no similar synergism takes place between the components of the isomer mixture Ia.

According to aspects of the present invention there is provided the selected isomer pair, an insecticidal composition comprising the same and a process for the preparation and the use thereof.

According to a still further aspect of the present invention there is provided a process for the preparation of the said new isomer pair. According to a particularly important aspect of the present invention there is provided a process for the preparation of the cypermethrin isomer-pair Ib which enables the highly economical preparation of an active ingredient having the same order of activity as the active ingredient which was hitherto available only by means of the very expensive isolation procedure of a pure and single cis isomer.

According to a further aspect of the present invention there is provided a synergistic insecticidal composition containing more than one active ingredients and being harmless to environment characterized by comprising in an amount of from 0.001 to 99% by weight a synthetic pyrethroid of the Formula /I/—namely substantially only the 1RtransS and 1StransR enantiomer-pair /Ib/ out of the possible eight isomers—optionally in admixture with an amount of up to 100% by weight of one or more activators and auxiliary agents, particularly antioxidants, stabilizing agents, wetting agents, emulsifying agents, dispersing agents, antifoam agents, diluents and/or fillers.

According to a further aspect of the present invention there is provided an isomer mixture Ib having a purity of at least 95% and comprising the 1RtransS and 1StransR enantiomer-pair of the Formula /I/.

The physical constants of said enantiomer-pair are as follows:

IR/KBr/$\nu_{c=o}$ = 1735 cm$^{-1}$

NMR/CDCl$_3$/$\delta$/ppm/=1.22, 1.27 CMe$_2$; 1.69d 1H C1; 2.32 m 1H C3; 5.6,d. 1H C1'; 6.39 s 1H alphaproton.

The said pure enantiomer-pair is a white crystalline material, never described in the prior art according to our best knowledge. The melting point of the 1:1 mixture of the isomers amounts to 81.0°–81.5° C. It is to be noted that the components Ig and Ii of the isomer-pair are not crystalline per se. Accordingly in addition to biological and economical advantages the combination of the present invention facilitates the process of manufacture, the formulation procedure, storing and method of treatment as well.

The isomer-pair Ib of the present invention is superior to the known combinations from the point of view of side effects, too. The new isomer-pair of the present invention has a very low toxicity on bees and does not damage useful entomophages and parasites (see biological Examples 4 and 5). This is due to the repellant effect, preferable persistence and suitable inherent activity of the active ingredient. As a result of the above advantageous properties the insecticidal composition of the present invention may be useful in integrated plant protecting technology (IPM=Integraded Pest Management).

The present invention is based on the further recognition that the enantiomer-pair of the present invention has substantially the same insecticidal activity as the enantiomer-pair Ia but is significantly less toxical on warm-blooded species. This is clearly substantiated by the selectivity index (7800) which is the quotient of approximative LD$_{50}$ toxicity values on rats (5000 mg/kg) and house fly (0.64 mg/kg). The said selectivity index of the enantiomer-pair Ia amounts to 50/0.45=111.

The isomer-pair Ib is less toxic to parasites than the isomer-pair Ia and this is of particular importance. For this reason the insecticidal composition of the present invention may be used more safely, because on the edge of the sprayed area and after treatment (i.e. in area treated with a small concentration of the active ingredient) the parasites and bees are not killed. The repellant effect of the isomer-pair Ib is outstandingly good, too.

The insecticidal compositions of the present invention comprising the isomer-pair Ib in admixture with known additives may be formulated in forms suitable for direct use.

The composition of the present invention may be ULV (ultra-low-volume) compositions, spray, dispersible powders, granules, wettable and other powders, stable emulsions etc. The said compositions are suitable for the pesticidal treatment of vegetables, orchards, fields of cereals and other large scale culrues. Due to the low toxicity the compositions of the present invention are particularly suitable for combating flying insects and pests having a hidden mode of life in households, stables and also for use in bathing of domestic animals and for the treatment of pasture.

According to a further aspect of the present invention there is provided the use of the said insecticidal compositions. It is preferred to use the said compositions under field comditions at a rate of 2-25 g of active ingredient per hectare.

The insecticidal compositions of the present invention may comprise in addition to the isomer-pair Ib activators and further synergists, e.g. piperonyl butoxide. The said additives strengthen the efficiency of the active ingredient without increasing the toxicity on warm-blooded species.

According to a preferred embodiment of the present invention there are provided dispersible granules comprising 1-99% by weight of the active ingredient in admixture with 99-1% by weight of suitable additives. As auxiliary agent e.g. 0.1-1% by weight of anionic and/or non-ionic surfactants may be used, such as alkali salts of alkyl-aryl sulfonic acids, alkali salts of condensation products of alkyl aryl sulfonic acids and formaldehyde, alkyl-aryl-polyglycol ether, sulfated long-chained alcohols, polyethylene oxides, sulfated fatty alcohols, fatty acid polyglycol esters and various other commercially available surfactants.

The insecticidal compositions of the present invention may also be formulated in the form of concentrates comprising preferably 5-50% by weight of the active ingredient in admixture with 50-95% by weight of additives which enable the formation of a stable emulsion when emulsifying the emulsion concentrate in or in the presence of water.

As additive 1-20% by weight of a tenside and/or 0.1-5% by weight of a stabilizing agent may be used and the mixture may be preferably filled up to 100% with an organic solvent.

It is preferred to use as tenside a mixture of anionic and non-ionic tensides having a HLB-value of 8-14. The following tensides may be preferably applied: calcium salts of alkyl aryl sulfonic acids, mono and diesters of phosphoric acid, nonyl and tributyl phenol polyglycol ethers, adducts of fatty alcohols and ethylene oxide, fatty acid polyglycol esters, ethylene oxide-propylene oxide block polymers etc.

As a solvent preferably mixtures of aromatic hydrocarbons (e.g. xylenes), cyclohexanol, butanol, methyl ethyl ketone, isopropanol etc. may be used.

The compositions of the present invention may also comprise further synergists which enable the reduction of the amount of the active ingredient. For this purpose preferably piperonyl butoxide may be applied.

According to a further aspect of the present invention there is provided a process for the preparation of a product comprising substantially only the enantiomer-pair 1RtransS+1SttransR (Ib) out of the eight possible isomers of the compounds of the Formula /I/ from mixtures comprising other isomers of further components, too.

The enrichment of cypermethrin mixtures in isomers having presumably a higher activity is described in several patent specifications. According to a patent publication [C.A. Vol. 95,(1981), Japanese Pat. KOKAI No. 57755/81] a crystalline cypermethrin isomeric mixture comprising 86.9% of Ic, 9.5% of Ia and 5.6% of Ib+Id is prepared by seeding a mixture comprising b 53.5% of Ic, 38.7% of Ia and 7.8% of Ib+Id. In this case it was expected that the biological activity of the compounds remaining in the mother-liquor would be higher.

It is the object of the other known procedures, too, to prepare cis isomer-pairs or substances enriched in cis isomer-pairs. According to a known process a mixture of enantiomer-pairs Ia and Ic is subjected to epimerisation to convert the Ic enantiomer-pair into Ia enantiomer-pair and to produce the known alphamethrin and decamethrin, respectively, by assymmetrical transformation [Chem. and Ind., March 19, 1985, 199-204; British patent application No. 80 13308; EP No. 0 067461; Dutch Pat. No. 888431, see Derwen 79766D]

Prior art is silent in teaching any methods directed to the preparation of trans isomers.

According to a further aspect of the present invention there is provided a process for the preparation of an isomer mixture Ib consisting substantially of only the enantiomer-pair 1RtransS and 1StransR—i.e. substantially only two out of the eight possible isomers of the compounds of the Formula /I/—from mixtures comprising also other isomers of the Formula /I/ which comprises a. preparing a saturated solution from a mixture comprising the desired isomers in admixture with further possible isomers with a protic or apolar aprotic inert organic solvent, seeding the solution with a seeding crystal consisting of the enantiomer-pair 1RtransS+1-StransR and isolating the precipitated crystals at a temperature between +30° C. and −30° C.; or b. seeding a melt of a mixture comprising the desired isomers in admixture with further possible isomers at a temperature between 10° C. and 60° C. with a seeding crystal consisting of the 1RtransS+ +1StransR enantiomer-pair, crystallizing at a temperature between 30° C. and −10° C., and if desired suspending the mixture thus obtained in a protic or apolar aprotic organic solvent at a temperature between −10° C. and −20 C. and isolating the separated crystals; or c. subjectiong a mixture comprising the desired isomer-pair Ib in admixture with further possible isomers to chromatography in an organic solvent preferably on a silica gel or Kieselguhr adsorbent; or d. dissolving a mixture comprising trans isomers of the compounds of the Formula /I/ in a protic or apolar aprotic solvent, seeding the solution with a seeding crystal consisting of the enantiomer-pair 1RtransS+1-StransR /Ib/, isolating the precipitated crystalline product Ib, and thereafter if desired epimerising the mixture comprising Ib+Id being present in the motherlye with an organic or inorganic base and if desired repeating the said step and/or the crystallizing step; or e. dissolving the mixture comprising the trans isomers in a secondary or tertiary organic amine base comprising 4-9 carbon atoms—optionally by adding an organic solvent—and seeding the solution thus obtained with a seeding crystal consisting of 1RtransS+1StransR isomers and thereafter isolating the precipitated crystals.

According to variants a/ and e/ of the process of the present invention one may preferably proceed by using a $C_{1-12}$ hydrocarbon, $C_{1-6}$ chlorinated hydrocarbon, $C_{1-5}$ dialkyl ether or $C_{1-10}$ alcohol as organic solvent. The said solvents may be straight or branched chained, and cyclic and alicyclic, respectively.

It is preferred to carry out seeding with a seeding crystal in the presence of an antioxidant—particularly tertiary butyl hydroxy toluene or 2,2,4-trimethyl-quinoline—and to use ethanol, isopropanol, petroleum ether or hexane as solvent.

According to variant d/ of the process of the present invention it is preferred to use a $C_{4-10}$ alkane, $C_{5-10}$ cycloalkane, $C_{1-8}$ alkanol and/or $C_{5-8}$ cycloalkanol or a mixture thereof as solvent. One may particularly advantageously use hexane, petroleum ether cyclohexane, methanol, ethanol or isopropanol.

In the epimerization step ammonia, secondary or tertiary alkyl amines or cyclic amines may be used as basic substance. Thus one may preferably use triethyl amine, diethyl amine, morpholine, pyrrolidine, piperidine, diisopropyl amine, ephedrine, triethylene diamine, benzyl amine, n-butyl amine, secondary butyl amine, tetrabutyl ammonium hydroxide, sodium hydroxide, potassium tertiary butylate, sodium isopropylate or an ion-exchanging resin comprising a quaternary ammonium compound or a catalytic amount of an amine having a large molecular weight.

As solvent it is preferred to use methanol, ethanol, isopropanol, petroleum ether or hexane.

The said reaction variants may be particularly economically used if the total munufacturing line comprises the use and preparation of isomers of the Formula /I/ other than Ib, too.

If synthetic cypermethrin manufacturing process makes it possible and if it is the amined object of the invention to manufacture only a mixture of trans cypermethrin by means of one of the esterifying procedures, variant e/ of the process of the present invention is particularly suitable for the economical manufacture of isomer-pair Ib. According to the said variant e/ namely the complete amount of the trans mixture is converted into the desired enantiomer-pair Ib.

According to variant e/ it is preferred to use triethyl amine, morpholine, pyrrolidine, piperidine, diisopropyl amine, ephedrine or secondary butyl amine as organic amine base.

It was a pre-condition of the feasibility of variant e/ to provide and prepared highly pure seeding crystals having a purity over 95% and melting above 80° C. from the non-crystallizing pure isomers Ii and Id. This enables the aimed directed asymmetrical transformation.

One may proceed furtheron preferably by dissolving the mixture in the amine in the presence of an organic solvent. For this purpose the solvents enumerated by variant a may be used.

According to variant a one may proceed by dissolving the isomer mixture of trans cypermethrins—comprising the 1RtransS, 1StransR, 1RtransR and 1StransS isomers—in triethyl amine. Crystalline starting materials are dissolved at a temperature between 40° C. and 70° C. and the solution obtained may be filtered. An oily cypermethrin mixture may be dissolved at room temperature as well.

Crystallization of the 1RtransS+1StransR isomer-pair may be carried out by seeding the solution at room temperature with crystals of a 1:1 mixture of the 1RtransS and 1StransR isomers (recommended purity 99.8%) and thereafter subjecting the mixture thus obtained to crystallization at a temperature between 0° C. and 20° C. with or without stirring. The precipitated crystals are separated by filtration or centrifuging and the mother liquor adhered to the surface of the crystals is washed off with an alkane (preferably a solvent of the cycloalkane type particularly petroleum ether). The united mother liquor are completely concentrated. The said crystallization procedure may be repeated. The asymmetrical transformation may be preferably accomplished in a dry inert gas (preferably nitrogen) atmosphere.

According to the above process a 1RtransS+1StransR isomer-mixture having a purity of about 95% may be prepared with a yield of 80% per step. The purity may be increased to 99-99.5% by means of further recrystallization from an alcohol, particularly isopropanol.

If the base serves as solvent, too, it is preferred to use an amine base having a water content not higher than 0.2-0.4%. Cis isomer contaminations of the trans cypermethrin mixture used as starting material may decrease the yield.

INDUSTRIAL APPLICABILITY

The insecticidal compositions of the present invention are harmless to environment and can be used particularly in household and stables for combating flying insects and pests having a hidden mode of life and also for bathing domestic animals and for the treatment of pasture.

MODES OF CARRYING OUT THE INVENTION

Further details of the present invention are to be found in the following chemical and biological examples without limiting the scope of protection to the said Examples.

Chemical Examples

EXAMPLE 1

10 g of a cypermethrin mixture consisting of 18.2% of Ia, 21.8% of Ic, 26.8% of Ib and 33.2% of Id are dissolved in 50 ml of a 95:5 mixture of n-hexane and tetrahydrofurane. The solution is subjected to chromatography on a column comprising 500 g of silica gel G. 25 ml fractions are collected by using a 95:5 mixture of n-hexane and tetrahydrofurane as eluting agent. Fractions corresponding to an $R_f$ value of 0.2 are collected (as TLC running mixture a 95:5 mixture of n-hexane and tetrahydrofurane is used). The said fractions are evaporated in vacuo. The residue thus obtained (2.9 g) is dissolved in 29 ml of ethanol at 45° C. and crystallized at 0° C. The precipitated product is filtered off, washed twice with 10 ml of icecold ethanol each and dried in vacuo. Thus 2.6 g of a white crystalline product are obtained, mp: 80.2° C.

Analytical characteristic data:

$R_f$=0.2 (Kieselguhr G plate, 95:5 mixture of n-hexane and tetrahydrofurane)

IR/KBr/$\nu_{c=o}$=1735 cm$^{-1}$

NMR/CDCl$_3$/δ/ppm/=1.22, 1.27, CMe$_2$; 1.69, d, 1H C1: 2.32, m, 1H C3; 5.6, d, 1H C1'; 6.39, s, 1H, C alphaproton.

EXAMPLE 2

To 10 g of a crystalline trans cypermethrin mixture (comprising 53.9% of 1RtransR and 1StransS isomers and 43.3% of Ig isomers according to gas chromatography) 15 ml of anyhdrous triethyl amine are added. The mixture is heated under nitrogen and under constant stirring to 60° C., whereupon the solution is quickly filtered and cooled to 30° C. The clear colorless solution thus obtained is seeded with a seeding crystal of a 1:1 mixture of Ib isomers, cooled to room temperature and allowed to crystallize for a day. The mixture is filtered cold. The product is dried at room temperature. Thus 8.4 g of a snow-white crystalline product are obtained. Mp.: 79.5°-80.5° C. According to gas chromatographic analysis the product comprises 95% of a 1:1 mixture of the desired Ib isomers. The mother liquor is evaporated. On repeating the above steps 1.05 g of white crystalline product are obtained as second crops, mp.: 79°-80° C.

The combined product is recrystallized from 50 ml of isopropanol. 8.5 g of a snow-white crystalline product are obtained as first crops, mp.: 80.5° C., active ingredient content 98%. On further recrystallization 7.5 g of a crystalline product are obtained, mp.: 81.5° C., active ingredient content above 99.5%.

Ir/KBr/$\nu_{c=o}$=1735 cm−1

NMR/CDCl$_3$/δ/ppm/=1.22, 1.27 CMe$_2$; 1.69, d, 1H C1; 2.32, m, 1H C3; 5,6, d, 1H C1'; 6.39, s, 1H, C alphaproton.

EXAMPLE 3

100 g of an oily crude (purity 95%) trans cypermethrin mixture (comprising 48% of 1RtransR and 1StransS isomers and 47% of ib isomers according to gas chromatography are dissolved in a solution of 150 ml of anhydrous triethyl amine and 0.2 g of tertiary butyl hydroxy toluene under stirring. The solution is quickly filtered, seeded, twice crystallized and recrystallized in an analoguous manner to Example b 2. Thus 82 g of snow-white crystalline isomer pair Ib are obtained, mp.: 80°–80.5° C., active ingredient content 97.5%.

EXAMPLE 4

10 g of oily trans cypermethrin mixture (comprising 85% of 1RtransR and 1StransS isomers and 14% of Ib isomers) are dissolved in 15 ml of anhydrous triethyl amine under stirring at room temperature, whereupon the solution is filtered and crystallized as described in Example 2. Thus 8 g of snow-white crystalline isomer mixture Ib are obtained, mp.: 79°–80.5° C.

EXAMPLE 5

10 g of crystalline trans-cypermethrin (comprising 52% of 1RtransR and 1StransS isomers and 47% of Ib isomer-pair) are dissolved in 15 ml of tri-n-propyl amine at 50° C. The solution is filtered, cooled to 30° C. and seeded with a seeding crystal consisting of a 1:1 mixture of the Ib isomers. The mixture is allowed to crystallize for 48 hours. Thus 8.2 g of a snow-white crystalline product are obtained, mp.: 78°–80° C. Purity 95% (according to gas chromatographic analysis).

EXAMPLE 6

One proceeds according to Example 5 except that 15 ml of tributyl amine are used as base. Thus 7.5 g of snow-white crystalline isomer-pair Ib are obtained, mp.: 77°–79° C., purity 93%.

EXAMPLE 7

One proceeds according to Example 5 except that 15 ml of triisopropyl amine are used as base. Thus 7.5 g of snow-white crystalline isomer-pair Ib are obtained, mp.: 78°–80° C., purity 95.5%.

EXAMPLE 8

One proceeds according to Example 5 except that 15 ml of diisopropyl amine are used as base. Thus 8.0 g snow-white crystalline isomer-pair Ib are obtained, mp.: 78°–80° C., purity 95.5%.

EXAMPLE 9

10 g of trans cypermethrin (comprising 48% of 1RtransS and 1StransR isomers and 49% of Ib isomer-pair) are dissolved in 50 ml of isopropanol under stirring and heating whereupon 2 ml of an aqueous ammonium hydroxide solution are added (specific weight 0.880 g/ml). The solution is seeded with seeding crystals of the isomer-mixture Ib, stirred at 20° C. for 24 hours, cooled to 0°–5° C., and stirring is continued at this temperature. The suspensiton is filtered, the product is washed with isopropanol and petrolether and dried. Thus 6 g of white crystalline isomer-pair Ib (1:1) are obtained, mp.: 78°–79° C., purity 92% (GC analysis). From the mother-lye 1.5 g of white crystalline product are obtained as second crops. Mp.: 78°–79° C. The composition of the second crop is identical with that of the crystals of the first generation.

EXAMPLE 10

10 g of trans cypermethrin (comprising 54% of 1RtransS and 1StransR isomers and 45% of isomers Ib) are dissolved in 100 ml of petrolether (b.p.:60°–80° C.) whereupon 1 ml of a 0.5 molar sodium carbonate solution and a 1:1 vol. mixture of water and methanol comprising 10 w/v of tetrabutyl ammonium bromide are added. The solution is seeded with a seeding crystal according to Example 2, allowed to crystallize for 4 says, filtered, washed with petrolether and dried. Thus 6.8 g of white crystalline isomer-pair Ib are obtained, mp.: 78°–80° C., purity 95%, /GC analysis/.

EXAMPLE 11

10 of crystalline trans cypermethrin (comprising 52% of 1RtransS and 1StransR isomers and 47% of 1RtransR and 1StransS isomers) are disolved in 100 ml of petrolether at 50°–60° C. To the solution 0.02 g 2,6-di-tertiary butyl-4-methyl-phenol is added. After filtration the filtrate is seeded at 30° C. with seeding crystals consisting of a 1:1 mixture of the Ib isomers. Crystallization is accomplished as disclosed above. Thus 3.8 g of snow-white crystalline isomer-pair Ib (1:1) are obtained, mp.:77°–79° C., purity 93%. On recrystallization from petrolether the melting point rises 80.5° C. The crystalization mother liquor is epimerized in a separate step.

EXAMPLE 12

10 g of crystalline trans cypermethrin (comprising 45% of 1RtransS and 1StransR isomers and 53% of 1RtransR and 1StransS isomers) are disolved in 75 ml of isopropanol of 50°–60° C. The solution is treated in an analogous manner to Example 11. Thus 3.6 g snow-white crystalline isomer-pair Ib are obtained. According to gas chromatography analysis the purity of the 1:1 amounts to 94%. Mp.: 80° C. Further recrystallization is accomplished as described in Example 2. Thus a product having an active ingredient content above 99% is obtained. The crystallization mother liquor is epimerized in a separate step.

EXAMPLE 13

Into an apparatus equipped with a stirrer the mother liquor obtained according to Example 11 (a solution enriched in isomer Id) is introduced and 1 g of Dowex Type 2×4 mesh (serva) basical ion-exchanging resin are added. The heterogenous suspension is stirred at 40° C. for 12 hours, filtered, washed twice with 2 ml os isopropanol each. According to gas chromatoraphy the solution comprises 41% of Ib isomer-pair and 46% of Id isomer. The soluton is evaporated and crystallized as described in Example 11.

EXAMPLE 14

One proceeds according to Example 13 except that petroleum ether is used as solvent. According to gas chromatographic analysis the solution comprises 39% of Ib isomer and 56%of the 1RtransR and 1StransS isomers.

EXAMPLE 15

10 g of colorless oily cypermethrin (comprising 30% of Ib, 31% of 1d, 18% of Ia and 21% of Ic) are seeded with seeding crystals of a 1:1 mixture of the Ib isomers and allowed to crystallize at 7° C. for a week. The viscous crystalline oil obtained is cooled to −15° C., suspended in 10 ml of a 1:1 mixture of isopropanol and diisopropyl ether cooled to −15° C. and filtered cold. The crystals thus obtained are washed with 5 ml of icecold isopropanol and dried at room temperature. Thus 2 g of white crystalline product Ib are obtained, mp.: 78°–80° C., purity 96% (GC). On recrystallization from 13 ml of hexane 2.25 g of a snow-white crystalline product are obtained, mp.: 80°–81° C., active ingredient content 99%.

EXAMPLE 16

10 g of cypermethrin (comprising 30% of Ib, 31% of Id, 18% of Ia and 21% of Ic) are dissolved in 100 ml of warm isopropanol whereupon 0.02 g of 2,5-di-tertiary butyl-4-methyl-phenol is added. The solution is clarified with 0.2 g of charcoal, filered warm and the filtrate is seeded at 30° C. with a seeding crystal consisting of a 1:1 mixture of the Ib isomers. The mixture is allowed to crystallize at 10° C. for 24 hours, at 0° C. for 48 hours and finally at −5° C. for 24 hours (crystallization is accomplished so that an oily separation of the product should be avoided). The crystals are filtered cold, washed with isopropanol and dried at room temperature. Thus 2.6 g of snow-white crystalline Ib isomer-pair (1:1) are obtained, mp.: 78°–80° C., purity 95%. On recrystallization from hexane 2.3 g of a snow-white crystalline product are obtained, mp.: 80°–81° C., active ingredient content 99%.

Formulation examples

EXAMPLE 17

Emulsifiable concentrates (EC) are prepared by admixing the following components:

| Component | Amount, kg/kg |
|---|---|
| 10 EC | |
| Isomer-pair Ib | 0.105 |
| Cyclohexanol | 0.290 |
| Atlox 3386 B | 0.020 |
| Atlox 3400 B | 0.045 |
| Odorless mineral oil | 0.540 |
| 5 EC | |
| Isomer-pair Ib | 0.050 |
| Cyclohexanol | 0.290 |
| Atlox 3386 B | 0.020 |
| Atlox 3400 B | 0.045 |
| Colorless mineral oil | 0.595 |

In a dose of 20 g of active ingredient/ha the composition 5 EC gives the same protection against Colorado beetle as a preparation of identical composition but comprising isomer Ia (alphametrine composition).

EXAMPLE 18

A solution of 1.5 g of isomer-pair Ib and 1.5 g of fatty alcohol polyglycol ether is homogenized in a powder homogenizer with 30 g of synthetic silicic acid (Wessalon S), 60 g of talc (pH 7.1), 5 g of saccharose and 3.35 g of dodecyl benzene sulfonic acid. Thus a thin flowing powder is obtained.

EXAMPLES 19

20 g isomer-pair Ib are diluted with 2 g of ethanol. The solution is admixed in a powder homogenizer with 5 g of calcium lignosulphonate, 5 g of nonyl-phenyl polyglycol ether (EO=20) and 70 g of calcium carbonate. The product thus obtained is ground in an Alpine 100 type mill. According to CIPAC the floatability amounts to 81%; wetting time=18 seconds.

Biological Examples

EXAMPLE 20

The comparative activity tests of enantiomer-pairs Ia and Ib on bean weevil (*Acanthoscelides obtectus*), flour-beetle (*Tribolium confusum*) and sheep maggot fly (*Lucilia sericata*) show that enantiomer-pair Ib is more active than enantiomer-pair Ia. The results are summarized in Table 1.

TABLE 1

| Species | Enantiomer pair | Dose (mg/disc) | | | | | |
|---|---|---|---|---|---|---|---|
| | | 0.02 | 0.07 | 0.22 | 0.67 | 2.0 | 6.0 |
| | | mortality % | | | | | |
| *A. obtectus* | Ia | 10 | 37 | 63 | 100 | 100 | 100 |
| (imago) | Ib | 32 | 55 | 87 | 100 | 100 | 100 |
| *T. confusum* | Ia | 0 | 18 | 51 | 100 | 100 | 100 |
| (imago) | Ib | 14 | 73 | 100 | 100 | 100 | 100 |
| *L. sericata* | Ia | 0 | 30 | 29 | 57 | 60 | 65 |
| (imago) | Ib | 22 | 55 | 70 | 75 | 100 | 100 |

The test is carried out as follows:

The stereoisomers are dissolved in a 1:2 mixture of mineral oil and acetone and filter paper discs (Whatman No. 1., diameter 9 cm) are impregnated with the corresponding dosage of the solution of the active ingredient. The acetone is allowed to evaporate and the insects are examined on filter paper discs placed into Petri dishes. Three parallels are used for each does and 15 animals are placed in each Petri dish. Mortality rate is determined after 24 hours. The corrected mortality % data are calculated by means of the Abbot formula.

EXAMPLE 21

In Table 2 the synergism between the stereoisomers of the enantiomer-pair Ib is proved. The test is carried out or *T. confusom* and the following results are obtained by contact method for various active ingredient doses.

TABLE 2

| Dose (mg/disc) | 0.11 | 0.33 | 1.00 | 3.00 |
|---|---|---|---|---|
| | mortality % | | | |
| 1StransR Ii | 0 | 0 | 71 | 90 |
| 1RtransS Ig | 80 | 94 | 100 | 100 |
| Ib enantiomer-pair | 90 | 100 | 100 | 100 |

The test is carried out according to the method described in Example 20.

EXAMPLE 22

In Table 3 the $LD_{50}$ values of the Ig and Ii isomers and those of the Ib isomer-pair are disclosed. The data are topically measured.

TABLE 3

| cypermethrin stereoisomers | $LD_{50}$ (ng/insect) *T. confusum* | | | $LD_{50}$ (ng/insect) *Musca domestica* | | |
|---|---|---|---|---|---|---|
| | measured | expected | synerg. factor | measured | expected | synerg. factor |
| Ig 1RtransS | 73.6 | — | — | 13.4 | — | — |
| Ii StransR | 1291.8 | — | — | 141.9 | — | — |
| Ib | 51.9 | 139.3 | 2.68 | 12.8 | 24.5 | 1.92 |

The above data prove the synergism between the trans isomers on both species.

The tests are carried out as follows:

a. *Musca domestica*

The active ingredients are dissolved in 2-ethoxyethanol (cellosolve) and 0.3 μl droplets of the solutions are applied onto the dorsal cuticulum of 3–5 days' old female house flies. 10 animals are used and 2 parallels are carried out for each dose. The tests are carried out for 5 dose levels between activity limts of 0% and 100%. After treatment the flies are placed into glass vials. Mortality is determined after 24 hours. Data are transformed to $\log_{10}$ dosage and probit mortality. $LD_{50}$ and confidence interval values are calculated by linear regression analysis of the log-probit data. The expected values required for the calculation of synergism are obtained by means of harmonic average. The synergistic factor is the quotient of the expected and measured values.

b. *T. confusum*

The active ingredients are dissolved in 2-ethoxyethanol and 0.3 μl droplets of the solutions are applied onto the abdominal side of 1–2 weaks' old images. Treatment is carried out with 2 parallels and 20 animals for each dose by using 5 dose levels in the range between activity limits of 0% and 100%. Evaluation and determination of $LD_{50}$ values and synergistic factors are carried out as described in Example 21.

EXAMPLE 23

Residual contact test on adults of *Apbidinus matricanae*

Adults of *A. matricariae* are exposed to residues of the active ingredients freshly applied on glass plates forming cages then the survivors are counted.

Treatments: test products and control treated with water.

Replicates: at least 3. Plot size (net): 1 cage.

Parasites of known age 24 hours are used.

The products are applied at 5–1 ppm concentration, to each of the glass plates.

10 females of *A. matricariae* are introduced into each cage and supplied with honey as food. The number of females surviving exposure is determined after 1.5 and 24 hours, in independent runs. Total number of survivors is calculated for each cage.

The results are summarized in Table 4.

TABLE 4

| | Concentration | | | |
|---|---|---|---|---|
| | 5 ppm | 1 ppm | | |
| | 1 h | 1 h | 5 h | 24 h hours |
| | | mortality % | | |
| Ia | 100 | 100 | 100 | 96 |
| Ib | 100 | 0 | 75 | 88 |
| control | 0 | 0 | 0 | 1.5 |

EXAMPLE 24

Direct contact test on pupae of *A. matricariae*

Mature pupae of *A. matricariae* on paprika leaves in Petri dishes are exposed to a direct spray of the active ingredients.

Two or three days before emergence paprika leaves with parasitized pupae are used. The leaves are laid on filter paper in a plastic Petri dish. The filter paper is moistened.

Application of treatment: see Example 23.

The pieces of leaf are transferred after treatment to clean Petri dish bottoms. The trays are stored in a climic chamber at 20° C. temperature, 70% relative humidity and a light-dark cycle of 16–8 h. Surviving pupae hatch after 2–3 days. The numbers of hatched and dead pupae are counted. Results are shown in Table 5.

TABLE 5

| | concentration/ppm/ | | | |
|---|---|---|---|---|
| | 30 | 10 | 5 | 1 |
| | | mortality % | | |
| Ib | 61.0 | 0 | 0 | 0 |
| deltametrin | 75.0 | 33.0 | 0 | 0 |
| control | 0 | 0 | 0 | 0 |

EXAMPLE 25

The active ingredients are dissolved in 2-ethoxyethanol and 0.3 μl droplets of the solutions are applied onto the abdominal sterna of potato beetle (*Leptinotarsa decemlineata*) imagos. The treatments are carried out by using two paralles and 10 insects for each dose. After treatment the insects are placed into Petri dishes and mortality is determined after 48 hours. The results are set forth in Table 6.

TABLE 6

| | Dose/μg/insect/ | | | |
|---|---|---|---|---|
| cypermethrin | 0.05 | 0.10 | 0.20 | 0.40 |
| enantiomers | | 24 hours' mortality % | | |
| Ib | 0 | 25 | 75 | 85 |
| cypermethrin | 0 | 20 | 45 | 75 |

EXAMPLE 26

*T. confusum* (confused flour-beetle) imagos are treated according to Example 20 and percental mortality is determined after 24 hours. The dose of piperonyl butoxide (referred to furtheron as "PBO") amounts to 0.5 mg/disc. The results are disclosed in Table 7. It $c_a$N be seen that enantiomer-pair Ib can be synergized at a higher level than isomer pair Ia.

TABLE 7

| | Dose (mg/disc) | | | | |
|---|---|---|---|---|---|
| Active ingredient | 0.4 | 0.2 | 0.1 | 0.05 | 0.025 |
| | | 24 hours' mortality % | | | |
| Ia | 96 | 53 | 12 | 0 | 0 |
| Ia + PBO | 100 | 58 | 16 | 0 | 0 |
| Ib | 100 | 85 | 51 | 10 | 0 |
| Ib + PBO | 100 | 91 | 68 | 39 | 9 |

EXAMPLE 27

The active ingredients are dissolved in 2-ethoxyethanol and the solutions are applied in the form of 0.2 μl droplets onto the back of fall webworm (*Hyphantria cunea*) of $L_7$-$L_8$ larvae stage. The treated worms are placed on strawberry leaves in Petri dishes. The test is carried out by using 5 doses; 2 parallels and 10 insects for each dose. The killed worms are counted after 24 hours and the percental morality rate is calculated. The results are summarized in Table 8.

TABLE 8

| | Dose/μg/larvae/ | | | | |
|---|---|---|---|---|---|
| cypermethrin | 0.023 | 0.047 | 0.094 | 0.188 | 0.375 |
| stereoisomers | | 24 hours' mortality | | | |
| Ib | 10 | 15 | 30 | 70 | 80 |
| cypermethrin | 0 | 0 | 25 | 50 | 75 |

EXAMPLE 28

From a 5 EC formulation according to Example 17 50-, 100-, 200-, 400-, 800-and 1600-fold diluted emulsions are prepared by diluting with water. 0.5 ml of the emulsions are sprayed onto glass plates whereupon after drying 10 Colorado beetles (*L. decemlineata*) imagos are placed on each glass plate and the insects are covered. The tests are carried out with 6 doses by carrying out 3 parallels for each dose. The killed insects are counted after 48 hours and the percental morality rate is calculated. The results are shown in Table 9.

TABLE 9

| 5 EC formulation | Dilution | | | | | |
|---|---|---|---|---|---|---|
| | 1600x | 800x | 400x | 200x | 100x | 50x |
| | | | mortality % | | | |
| cypermethrin | 0 | 17 | 33 | 50 | 67 | 83 |
| Ib | 0 | 13 | 37 | 57 | 87 | 100 |

EXAMPLE 29

The insecticidal effect is tested on been weevil (*Acanthoscelides obtectus*) imagos. The killed insects are counted after 24 hours and the percental mortality rate is calculated. The results are shown in Table 10.

TABLE 10

| 5 EC formulation | Dilution | | | | | |
|---|---|---|---|---|---|---|
| | 1600x | 800x | 400x | 200x | 100x | 50x |
| | | | mortality % | | | |
| cypermethrin | 0 | 3 | 10 | 20 | 43 | 60 |

TABLE 10-continued

| 5 EC formulation | Dilution | | | | | |
|---|---|---|---|---|---|---|
| | 1600x | 800x | 400x | 200x | 100x | 50x |
| | | | mortality % | | | |
| Ib | 3 | 10 | 20 | 37 | 53 | 67 |

What we claim is:

1. A synergistic insecticidal composition consisting of an effective component harmless to the environment, a synergistic mixture in an amount of 0.001 to 99% by weight of only the 1RtransS and 1StransR enantiomer pair of the synthetic pyrethroid of the Formula (I)

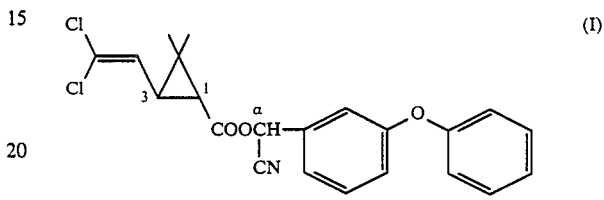

with the balance being an insecticidally compatible activator, antioxidant, stabilizer, wetting agent, emulsifying agent, dispersing agent, antifoam agent, diluent or filler.

2. The composition as defined in claim 1 wherein the 1RtransS and 1StransR enantiomer pair has a purity of at least 95% and the following IR andd NMR data:

IR (KBr) $\nu_{c=o}=1735$ cm$^{-1}$

NMR (CDCl$_3$)$\delta$(ppm)=1.22, 1.27, CMe$_2$; 1.69, d, 1H C1; 2.32 m, 1H C3; 5.6, d, 1H C1'; 6.39, s, 1H C alphaproton.

3. The composition as defined in claim 1 wherein the 1RtransS and 1StransR enantiomer pair has a melting point of 80.5°–81.5° C.

* * * * *

UNITED STATES PATENT AND TRADEMARK OFFICE
CERTIFICATE OF CORRECTION

PATENT NO. : 4,845,126

DATED : July 4, 1989

INVENTOR(S) : Gyorgy HIDASI et al

It is certified that error appears in the above-identified patent and that said Letters Patent is hereby corrected as shown below:

Col. 8, line 38, for "Ig" read "Ib";
Col. 9, line 47, for "Ib" read --Id--; and
Col. 9, line 65, for "Ib" read --Id--.

Signed and Sealed this

Thirtieth Day of April, 1991

Attest:

HARRY F. MANBECK, JR.

*Attesting Officer*          *Commissioner of Patents and Trademarks*